United States Patent [19]

Madrange née Dermain et al.

[11] 4,173,627
[45] Nov. 6, 1979

[54] HAIR LACQUER SPRAYS HAVING REDUCED INFLAMMABILITY

[75] Inventors: Annie Madrange née Dermain, Saint Germain en Laye; Henri M. de Montalembert, Boulogne; Pierre Meurice, L'Isle Adam; Jean-Louis Refregier, Boussy-Saint-Antoine, all of France

[73] Assignee: L'Oreal, Paris, France

[21] Appl. No.: 897,205

[22] Filed: Apr. 17, 1978

[30] Foreign Application Priority Data

Apr. 26, 1977 [FR] France ................................ 77 12569

[51] Int. Cl.² .............................................. A61K 7/11
[52] U.S. Cl. ..................................... 424/47; 252/305; 424/DIG. 1; 424/DIG. 2; 424/71
[58] Field of Search .................. 424/DIG. 1, DIG. 2, 424/47, 71; 252/305

[56] References Cited

U.S. PATENT DOCUMENTS

| 3,715,428 | 2/1973 | Quasius et al. | 424/47 |
| 3,790,664 | 2/1974 | Krochock et al. | 424/47 |
| 3,806,317 | 4/1974 | Viout et al. | 8/127.51 |

Primary Examiner—James O. Thomas, Jr.
Assistant Examiner—Vera C. Clarke
Attorney, Agent, or Firm—Brisebois & Kruger

[57] ABSTRACT

Hair lacquer compositions in pressurized containers are rendered less inflammable consistently throughout the emptying of the container by incorporating bromotrifluoromethane therein in an amount from 5 to 30% by weight based on the weight of the composition and providing the container with a valve provided with an inlet for additional gas.

10 Claims, No Drawings

HAIR LACQUER SPRAYS HAVING REDUCED INFLAMMABILITY

It is known that to maintain the hair in a proper shape it is current practice to use hair lacquers which one projects onto the head of the hair in the form of a fine aerosol spray. This aerosol is in general obtained by placing an alcoholic solution of the hair lacquer in a pressurized container and distributing the solution with the aid of a distribution valve which is provided with the pressurized container. The aerosol jet obtained from the pressurized container called an "aerosol bomb" should have, in order that the distribution is effected to the satisfaction of the user, specific characteristics relative to the dimensions of the jet and the dimensions of the droplets which constitute the aerosol. The pressurization of the "aerosol bombs" is currently effected using chlorofluoroalkanes which are mixed in the container with the lacquer solution which one desires to distribute and which represent a significant proportion of the liquid phase present in the aerosol bomb. During distribution, at the moment the liquid ejected comes into the atmosphere, there is a rapid or explosive vaporization of the chlorofluoroalkanes which contribute largely to the production in the atomized jet of droplets having dimensions very much reduced thus enabling one to satisfy the specific conditions required of the atomized jet. Amongst the chlorofluoroalkanes those most commonly used for the pressurization of aerosol bombs for hair lacquers are trichlorofluoromethane and dichlorodifluoromethane.

It is known, in particular for ecological reasons, that it would be preferable to avoid dispersing into the atmosphere significant quantities of trifluoromethane and dichlorodifluoromethane. Accordingly, one has been led to examine the possibility of distributing hair lacquers without using these chlorofluoroalkanes but retaining, nevertheless, the specific characteristics of the atomized jet which one wishes to obtain. It has already been proposed to replace the chlorofluoroalkanes by liquefied hydrocarbons such as butane, propane, isobutane and mixtures of them, dimethyl ether or a compressed gas capable of being dissolved at least partially in the liquid phase such as carbon dioxide or nitrous oxide. Independently of the difficulties which one encounters in conserving the geometric and dimensional characteristics necessary for the atomized jet it has been found that one encounters a not unimportant disadvantage as regards the inflammability of the atomized jet. In effect, the hair lacquers are generally resins dissolved in a mixture of alcohol and various solvents and these solutions, as they are atomized, have a considerable degree of inflammability; the inflammability of atomized alcohol and solvents has not been a significant problem in the past because the above-mentioned chlorofluoroalkanes represent the major proportion of the liquid phase in the aerosol container; these chlorofluoroalkanes are non-inflammable and they have the effect of a diluent thereby reducing the inflammability of the atomized jets to a tolerable level. However, if one eliminates the chlorofluoroalkanes by replacing them with other propellents the inflammability of the atomized jets becomes sufficiently significant to present a potential risk, above all where the propellant used is a liquefied hydrocarbon which is itself, very inflammable.

The present invention is, accordingly, intended to provide a way of reducing the inflammability of atomized jets of hair lacquers in the case where the lacquer solutions are propelled by liquefied hydrocarbons or by dimethyl ether. According to the present invention, one adds to the mixture contained in the pressurized vessel containing the hair lacquer solution bromotrifluoromethane which reduces inflammability which on being ejected in the gas phase in the atomized jet at the same time as the other products enables one to reduce considerably the inflammability of the aerosol jet and thus avoid dangers to the operator.

According to the present invention there is provided a pressurized container containing a hair lacquer composition partially in the gaseous phase and partially in the form of a single liquid phase, the composition containing at least one resin suitable for use as a hair lacquer, a liquid capable of dissolving the resin and a propellant which is partly in the gas phase in the interior of the container, said propellant phase generating the pressure in the container and comprising bromotrifluoromethane, characterized in that the bromotrifluoromethane is present in an amount from 5 to 30% by weight based on the total weight of the composition, the liquid phase is inflammable and the valve of the container comprises an inlet valve for additional gas supplying an atomizing device.

In a preferred embodiment one or more of the following features is present: the inlet valve for additional gas has a mass ratio of gas to liquid from 0.01 to 10%; the composition contains 10 to 85% by weight of propellant phase relative to the total weight of the composition; the propellant phase contains, as well as bromotrifluoromethane, volatile hydrocarbon, for example those which can be liquefied under pressure, such as butane, isobutane, propane and mixtures thereof, dimethyl ether and fluoroalkanes; if the propellant phase contains fluoroalkanes other than bromotrifluoromethane these other fluoroalkanes can also reduce the inflammability.

It should be noted that the propellant phase can be constituted exclusively by the bromotrifluoromethane provided that the compound is present in a sufficient amount to ensure by itself the propulsion of substantially the whole of the composition from the container. In other words, in the specified proportions, namely from 5 to 30% of bromotrifluoromethane, the lower end of the range corresponds to the case where the compound is not the only propellant and the upper part of the range corresponds to the case where the compound alone acts as the propellant or as the major constituent of the propellant phase.

In order to put the compositions according to the invention into effect one can use any valve of the specified type, for example the valve AR 74 produced by Reboul-Sofra, or the valve described in U.S. Pat. No. 3,061,203.

It will be appreciated that if the composition according to the invention, or an analogous composition containing an inflammability reducing agent, is ejected without using the special valve one obtains in all cases a reduction in the inflammability of the atomized jet but it has been found that this reduction is not very constant and, in particular, depending on the amount of material remaining in the pressurized container. Against this, if one uses the composition in the container according to the present invention using the inlet valve there is a reduction in the inflammability of the atomized jet which is completely reliable and constant, in particular throughout the emptying of the container. It is thought that this result is due to the fact that the gaseous part of the composition in the container contains a proportionally much larger amount of bromotrifluoromethane than the liquid part by reason of the fact that this compound has a boiling point of −57.6° C. There is thus, during emptying of the container, a repartitioning of the bromotrifluoromethane of the liquid phase to the gaseous phase progressively as the gaseous phase is ejected with the uptake of additional gas by the valve. As a result the content of bromotrifluoromethane in the gaseous phase ejected remains roughly constant during emptying. As the atomized jet is produced the aerosol droplets contain a certain proportion of bromotrifluoromethane which, on entering the atmosphere, vaporizes rapidly and provokes a very fine atomization; these droplets, at a given point in the atomized jet, are surrounded by a gaseous phase ejected by the valve for additional gas, this gas phase containing a substantially constant proportion of gaseous bromotrifluoromethane. Bearing in mind that the bromotrifluoromethane has, by itself, an inflammability reducing effect, it follows that the atomized jet is only slightly inflammable, not only by reason of the presence of the bromotrifluoromethane in the droplets but also by reason of the gaseous environment surrounding these droplets. The consistency of the lack of inflammability of the atomized jet is thus obtained by reason of the consistency of the composition surrounding the droplets in the jet, in spite of the fact that there is a variation in the production of bromotrifluoromethane in the liquid droplets ejected.

As indicated above, bromotrifluoromethane has, as well as inflammability reducing properties, a propellant function by reason of its low boiling point. Certain products present in the liquid phase for the resin of the composition can also have a propellant function. This is the case, in particular, if the liquid contains butane, isobutane, propane or mixtures thereof.

The liquid phase of the composition according to the present invention advantageously contains at least one of the following:

(a) a lower alkanol such as ethanol, propanol, isopropanol or butanol;

(b) a solvent such as 1,1,1-trichloroethane and methylene chloride;

(c) a diluent such as a ketone, in particular acetone and methylethyl ketone, an alkyl acetate, in particular methyl acetate or ethyl acetate, or a hydrocarbon, in particular a $C_3-C_7$ alkane.

The composition used in the present invention advantageously contains 0 to 94% of lower alkanol, 0 to 35% of solvent and 0 to 25% of diluent, all these percentages being by weight based on the weight of the composition as a whole.

Previously hair lacquer compositions have contained, in general, a high proportion of ethanol which one cannot replace, in spite of its high price, by more volatile solvents without increasing the inflammability of the atomized jet. The fact that the composition used in the present invention contains at least one inflammability reducing agent enables one to replace a part of the ethanol by a more volatile solvent such as butane, isobutane, propane, pentane, hexane or heptane without increasing the risks of inflammability; this replacement has, further, the advantage that for an atomized jet of given geometric and dimensional characteristics, one can diminish the wetting power of the atomized jet; this is of particular advantage bearing in mind the fact that the user of the pressurized container is able to distribute the hair lacquer composition without having the impression, during distribution, that the head is being moistened.

Further, if the propellant phase is constituted at least partially by an inflammable hydrocarbon the use of bromotrifluoromethane which assists the propulsion of the composition enables one to reduce the proportions of the inflammable hydrocarbon propellant in the composition; for example the use of 15% by weight of bromotrifluoromethane enables one, for a composition propelled by isobutane, to reduce the proportion of isobutane from 30% to 15%. One can see, therefore, that the use of bromotrifluoromethane enables one to reduce the inflammability of the atomized jet, not only by reason of the presence of the inflammability reducing agent itself but also because this enables one to reduce the proportion of inflammable propellant necessary for the ejection of the composition.

The resins which can be used in the compositions in the container of the present invention and which are anionic can, if desired, be at least partially neutralized with neutralizing agents such as sodium hydroxide, 2-amino-2-methyl-1-propanol, 2-amino-2-methyl-1,3-propanediol, triisopropanolamine and triethanolamine. The resins are preferably present in the composition in an amount from 0.5 to 10% by weight based on the total weight of the composition. These resins are typically as follows:

(a) The resins described in French Pat. No. 1,580,545 which are copolymers of:
(1) esters of unsaturated alcohols and short chain (i.e. less than 8 carbon atoms) saturated carboxylic acids or esters of short chain saturated alcohols and unsaturated acids;
(2) unsaturated acids;
(3) esters of long chain (i.e. at least 8 carbon atoms) acids and unsaturated alcohols or esters of unsaturated acids as defined in paragraph (2) and a $C_8-C_{18}$ alcohol or alkyl vinyl ethers or α-olefins.

(b) The resins described in French Pat. No. 1,584,053 which are copolymers of at least one unsaturated ester monomer and at least one unsaturated acid monomer.

(c) The resins described in Fench Pat. No. 75-09892 which are terpolymers of crotonic acid, vinyl acetate and allyl or methallyl esters.

(d) Polyvinylpyrrolidone commercialized under the tradename "PVP K 30" by General Anilin Film Corporation (GAF).

(e) The copolymers of vinylpyrrolidone and vinyl acetate commercialized under the names "PVP/VA E 335", "PVP/VA S 630" and "PVP/VA E 535" by GAF.

(f) The copolymers of vinyl pyrrolidone and vinyl acetate commercialized under the tradename "LUVISKOL VA 37 E", "LUVISKOL 64" and "LUVISKOL 28 I" by BASF.

(g) The copolymers of vinyl acetate and crotonic acid commercialized under the tradename "28.13.10" by National Starch or "ARESIL 83.12" by Montanoir or "ARISTOFLEX C" by Hoechst.

(h) The copolymers of methylvinylether and semiesterified maleic anhydride such as those commercialized under the tradenames "GANTREX ES 225", "GANTREZ 335 I", "GANTREZ ES 425" and "GANTREZ ES 435" by GAF.

(i) The amphoteric acrylic copolymers commercialized under the tradename "AMPHOMER" by National Starch.

(j) The vinyl terpolymers containing an acrylic ester group and a carboxylic acid group commercialized under the tradename "VEM 640" and "VEM 649" by De Barr.

(k) The terpolymers of vinyl acetate, crotonic acid and vinyl neodecanoate commercialized under the tradename "28.29.30" by National Starch.

The compositions contained in the container of the present invention can also contain in the liquid phase a variety of other ingredients such as plasticizers, silicones, lanolin derivatives and perfumes.

It will be appreciated that in all cases the use of bromotrifluoromethane in the composition enables one to reduce considerably and constantly the risks of inflammability of the atomized jet obtained with those compositions. The inflammability measurements mentioned below were carried out according to the method described by Lefebvre at the Congress of Aerosols in Berlin in 1967 using the apparatus of Dr. Roth; according to this method, an atomised jet is passed over a flame and the length of the flame produced by the projection of the aerosol downstream of the ignition flame and, if it is produced, the extension of the flame upstream (blow back) of the ignition flame is measured. The compositions corresponding to the different atomized jets are classed into six classes defined in the following Table:

| Class | Description | Length of the flame L in cm | Blow back |
|---|---|---|---|
| 1 | Not inflammable | L < 5 | Without blow back |
| 2 | Combustible | 5 < L < 25 | Without blow back |
| 3 | Combustible with blow back | 5 < L < 25 | With blow back |
| 4 | Slightly inflammable | L > 25 | Without blow back |
| 5 | Inflammable | L > 25 | With blow back |
| 6 | Very inflammable | L > 25 | With blow back and persistence of the flame after extinction of the ignition flame |

The following Examples further illustrate the present invention. In these Examples, the characteristics of inflammability are given using the classes defined above comparing the characteristics of compositions according to the present invention with corresponding compositions in which the bromotrifluoromethane is replaced by a chlorofluoroalkane used in known fashion as a propellant for hair lacquer compositions, the vessel and the valve remaining the same in the two cases. In all the Examples, the resins are defined by their trade names.

EXAMPLE 1

An aerosol container having a valve of the type AR 74 is filled with the following composition:
Resin "28.13.10" neutralized with 2-amino-2-methyl-1-propanol: 2.5 g
Plasticizer: 0.5 g
Methylene chloride: 35 g
Bromotrifluoromethane: 15 g
Dibromo-1,1,2,2-tetrafluoroethane: 5 g
Isobutane: 20 g
Ethanol: 22 g This composition corresponds to class 4 while the same composition without the bromotrifluoromethane corresponds to class 6.

EXAMPLE 2

In an aerosol container having a valve of the type AR 74 the following compositions are introduced:
Resin "GANTREZ ES 425" Neutralized with triisopropanolamine: 2 g
Plasticizer: 0.5 g
Bromotrifluoromethane: 20 g
Trichloroethane: 10 g
Methylene chloride: 25 g
Butane/propane (65/35): 10 g
Ethanol: 32.5 g This composition corresponds to class 4 while the same composition without bromotrifluoromethane corresponds to class 6.

EXAMPLE 3

The following composition is introduced into an aerosol container having a valve of the type AR 74:
Resin "AMPHOMER" neutralized with 2-amino-2-methyl-1-propanol: 2.5 g
Trichloroethanol: 35 g
Bromotrifluoromethane: 15 g
Asymmetric dibromohexafluoropropane: 5 g
Dimethyl ether: 25 g
Ethanol: 17.5 g This composition corresponds to class 4 while the same composition without the bromotrifluoromethane corresponds to class 6.

EXAMPLE 4

The following composition was introduced into an aerosol container with a valve of the type AR 74:
Resin "28.13.10" neutralized with 2-amino-2-methyl-1-propanol: 3 g
Trichloroethane: 35 g
Pentane/isopentane (80/20): 20 g
Bromotrifluoromethane: 20 g
Ethanol: 22 g This composition corresponds to class 2 while the same composition without bromotrifluoromethane corresponds to class 6.

EXAMPLE 5

The following composition is introduced into an aerosol container having a valve of the type AR 74:
Resin "28.29.30" neutralized with triisopropanolamine: 3.5 g
Ethanol: 21.5 g
Methylene chloride: 35 g
Dimethyl ether: 25 g
Bromotrifluoromethane: 15 g This composition corresponds to class 2 while the same composition without bromotrifluoromethane corresponds to class 6.

EXAMPLE 6

The following composition is introduced into an aerosol container having a valve of the type AR 74:
Resin "GANTREZ ES 425" neutralized with 2-amino-2-methyl-1-propanol: 2 g
Plasticizer: 0.5 g
Ethanol: 27.5 g
Trifluoroethane: 35 g
Dibromo-1,1,2,2-tetrafluoroethane: 15 g Bromotrifluoromethane: 20 g This composition corresponds to class 2 while the same composition without bromotrifluoromethane corresponds to class 5.

We claim:

1. In the known type of pressurized container which contains a hair setting composition that is partially in the gaseous phase and partly in a single liquid phase, said composition containing:
   (a) at least one resin suitable for use as a hair lacquer,
   (b) an inflammable liquid phase for dissolving the resin,
   (c) a propellant phase of which a part is in the form of a gas in the body of the pressurized container, said propellant phase providing the pressurization in the container,
   the improvement comprising
   (1) utilizing a propellant comprising bromotrifluoromethane,
   (2) the bromotrifluoromethane being present in an amount ranging from about 5 to 30% by weight based on the total weight of the composition, and
   (3) the valve of the pressurized container being a valve provided with an inlet for supplying additional gas.

2. A container according to claim 1 in which the inlet valve for additional gas has a mass ratio of gas to liquid from about 0.01 to 10%.

3. A container according to claim 1 in which said propellant phase comprises about 10 to 85% by weight based on the total weight of the composition.

4. A container according to claim 1 in which the propellant phase of the composition contains at least one volatile hydrocarbon which is selected from the group consisting of (a) butane, (b), isobutane, (c) propane, (d) mixtures of butane, isobutane and propane, (e) dimethylether and (f) a difluoroalkane other than bromodifluoromethane.

5. A container according to claim 1 in which the propellant phase consists exclusively of bromotrifluoromethane.

6. A container according to claim 1 in which the liquid phase contains at least one lower alkanol.

7. A container according to claim 1 in which the liquid phase contains at least one material selected from the group consisting of ethanol, propanol, isopropanol, butanol, 1,1,1-trichloroethane, methylene chloride, acetone, methylethyl ketone, methyl acetate, ethyl acetate and a $C_3$–$C_7$ alkane.

8. A container according to claim 1 in which the resin is anionic and has been at least partially neutralized by a neutralizing agent selected from the group consisting of sodium hydroxide, 2-amino-2-methyl-1-propanol, 2-amino-2-methyl-1, 3-propanediol, triisopropanolamine and triethanolamine.

9. A container according to claim 1 in which the resin is present in an amount from about 0.1 to 10% by weight based on the total weight of the composition.

10. A container according to claim 1 in which said composition additionally contains at least one material selected from the group consisting of a silicone, a lanolin derivative and a perfume.